(12) United States Patent
Sullivan et al.

(10) Patent No.: US 10,849,555 B1
(45) Date of Patent: Dec. 1, 2020

(54) DEVICES AND SYSTEMS FOR CORRECTING ERRORS IN BLOOD PRESSURE MEASUREMENTS

(71) Applicants: Thomas J. Sullivan, San Jose, CA (US); Ravi K. Narasimhan, Sunnyvale, CA (US); Rui Qiao, Cupertino, CA (US); Derek Park-Shing Young, Fremont, CA (US); Robert K. Montgomery, II, Cupertino, CA (US); Mohsen Mollazadeh, Cupertino, CA (US); Zijing Zeng, San Jose, CA (US); Vasco D. Polyzoev, Cupertino, CA (US); Richard C. Kimoto, Fremont, CA (US)

(72) Inventors: Thomas J. Sullivan, San Jose, CA (US); Ravi K. Narasimhan, Sunnyvale, CA (US); Rui Qiao, Cupertino, CA (US); Derek Park-Shing Young, Fremont, CA (US); Robert K. Montgomery, II, Cupertino, CA (US); Mohsen Mollazadeh, Cupertino, CA (US); Zijing Zeng, San Jose, CA (US); Vasco D. Polyzoev, Cupertino, CA (US); Richard C. Kimoto, Fremont, CA (US)

(73) Assignee: Apple Inc., Cupertino, CA (US)

( * ) Notice: Subject to any disclaimer, the term of this patent is extended or adjusted under 35 U.S.C. 154(b) by 411 days.

(21) Appl. No.: 15/274,204

(22) Filed: Sep. 23, 2016

Related U.S. Application Data

(60) Provisional application No. 62/234,509, filed on Sep. 29, 2015.

(51) Int. Cl.
*A61B 5/02* (2006.01)
*A61B 5/00* (2006.01)
(Continued)

(52) U.S. Cl.
CPC ........ *A61B 5/6824* (2013.01); *A61B 5/02141* (2013.01); *A61B 5/02225* (2013.01);
(Continued)

(58) Field of Classification Search
CPC ..... A61B 5/6824; A61B 5/7225; A61B 5/681; A61B 5/02255; A61B 5/02225; A61B 5/02141; A61B 5/02233
See application file for complete search history.

(56) References Cited

U.S. PATENT DOCUMENTS 4,331,154 A * 5/1982 Broadwater .......... A61B 5/021
600/490
5,065,765 A 11/1991 Eckerle et al.
(Continued)

FOREIGN PATENT DOCUMENTS

CN 201847682 6/2011

OTHER PUBLICATIONS

Hu, et al., "Temporal and Spatial Properties of Arterial Pulsation Measurement Using Pressure Sensor Array", Evidence-based Complementary and Alternative Medicine, vol. 2012, Article ID 745127, 2011, 9 pages.
(Continued)

*Primary Examiner* — Navin Natnithithadha
*Assistant Examiner* — Andrey Shostak
(74) *Attorney, Agent, or Firm* — Kilpatrick Townsend & Stockton LLP

(57) ABSTRACT

The present disclosure generally relate s to blood pressure monitoring. In some embodiments, methods and devices for measuring a mean arterial pressure and/or for monitoring blood pressure changes of a user are provided. Blood pressure measured by one or more pressure sensors may be adjusted using one or more correction factors. The use of the one or more correction factors disclosed herein may allow
(Continued)

for more compact, convenient, and/or accurate wearable blood pressure measurement devices and methods. In particular, wrist-worn devices may be provided which are less bulky than current devices and may facilitate more frequent and accurate blood pressure monitoring.

18 Claims, 7 Drawing Sheets

(51) Int. Cl.
    *A61B 5/021*     (2006.01)
    *A61B 5/022*     (2006.01)
    *A61B 5/0225*     (2006.01)

(52) U.S. Cl.
    CPC ...... *A61B 5/02233* (2013.01); *A61B 5/02255* (2013.01); *A61B 5/681* (2013.01); *A61B 5/7225* (2013.01)

(56) References Cited

U.S. PATENT DOCUMENTS

| | | | |
|---|---|---|---|
| 5,273,046 A | 12/1993 | Butterfield et al. | |
| 5,908,027 A | 6/1999 | Butterfield et al. | |
| 6,730,038 B2 | 5/2004 | Gallant et al. | |
| 7,070,322 B1* | 7/2006 | Field | A44C 5/0053 |
| | | | 224/164 |
| 8,086,301 B2 | 12/2011 | Cho et al. | |
| 2002/0062086 A1 | 5/2002 | Miele et al. | |
| 2003/0149369 A1* | 8/2003 | Gallant | A61B 5/021 |
| | | | 600/485 |
| 2005/0034317 A1 | 2/2005 | Burandt et al. | |
| 2006/0079792 A1 | 4/2006 | Finburgh et al. | |
| 2008/0228089 A1 | 9/2008 | Cho et al. | |
| 2010/0069764 A1 | 3/2010 | Kang | |
| 2011/0214158 A1* | 9/2011 | Pasquero | G06F 21/35 |
| | | | 726/2 |
| 2012/0179067 A1* | 7/2012 | Wekell | A61B 5/0002 |
| | | | 600/587 |
| 2012/0316448 A1 | 12/2012 | Gu et al. | |
| 2013/0158418 A1 | 6/2013 | Mizukami et al. | |
| 2015/0112606 A1 | 4/2015 | He et al. | |
| 2015/0164351 A1 | 6/2015 | He et al. | |
| 2016/0037897 A1* | 2/2016 | Bataillou | A44C 5/20 |
| | | | 224/267 |
| 2016/0255944 A1* | 9/2016 | Baranski | A44C 5/0069 |

OTHER PUBLICATIONS

Liu, et al., "A Novel Flexible Pressure Sensor Array for Depth Information of Radial Artery", Sensors and Actuators A: Physical, vol. 272, Dec. 27, 2017, pp. 92-101.

Wang, et al., "A Compound Pressure Signal Acquisition System for Multichannel Wrist Pulse Signal Analysis", IEEE Transactions on instrucmentation and measurement, vol. 63, No. 6, Jun. 2014, pp. 1556-1565.

* cited by examiner

DEVICES AND SYSTEMS FOR CORRECTING ERRORS IN BLOOD PRESSURE MEASUREMENTS

CROSS REFERENCE TO RELATED APPLICATION DATA

The present application claims the benefit of U.S. Provisional Appln. No. 62/234,509 filed Sep. 29, 2015; the full disclosure which is incorporated herein by reference in its entirety for all purposes.

BACKGROUND OF THE DISCLOSURE

The present disclosure generally relates to the measuring and monitoring of blood pressure. More specifically, embodiments may determine and apply one or more correction factors for calculating or adjusting a measured blood pressure to provide for a more accurate blood pressure measurement. This may be particularly beneficial with blood pressure measurement devices that may be worn by a user that non-invasively measure and monitor blood pressure of a user.

Elevated blood pressure (a.k.a. hypertension) is an indicator for potential health issues. As a result, blood pressure measurement is a routine test in many medical examinations.

A person's blood pressure is a continuously changing vital parameter. As a result, blood pressure measurements during intermittent visits to a physician may be insufficient to detect some forms of hypertension. For example, hypertension can occur in a pattern that evades detection during a visit to the physician's office (in-office measurements). Common hypertension patterns include white coat hypertension (elevated only during a limited morning period of time), borderline hypertension (fluctuating above and below definitional levels over time), nocturnal hypertension (elevated only during sleeping hours), isolated systolic hypertension (elevated systolic pressure with non-elevated diastolic pressure), and isolated diastolic hypertension (elevated diastolic pressure with non-elevated systolic pressure). To detect such hypertension patterns, it may be beneficial to perform additional blood pressure measurements over time to obtain a more complete view of a person's blood pressure pattern and features. Although continuous measurement of blood pressure can be achieved by invasive means, for example, via an intra-arterial pressure sensing catheter, non-invasive blood pressure measurement approaches may be more preferable.

Current non-invasive blood pressure measurement approaches include ambulatory and home blood pressure measurement strategies. These strategies provide a more complete view of a person's blood pressure characteristics and are often employed in recommended/prescribed situations. Ambulatory blood pressure measurement is performed while the person performs daily life activities. Currently, ambulatory blood pressure measurements are typically performed every 20 to 30 minutes using large and bulky brachial oscillometric blood pressure measurement cuffs. Ambulatory blood pressure measurement may be recommended or prescribed where there is large variability in in-office blood pressure measurements, where a high in-office blood pressure measurement is measured in a person with otherwise low cardiovascular risk, when in-office and home blood pressure measurements vary, where resistance to drug treatment of high-blood pressure is noted or suspected, where hypotensive episodes are suspected, or where pre-eclampsia is suspected in pregnant women. Home blood pressure measurement includes isolated self-measurements performed by a person at home. Home blood pressure measurements may be recommended where information is desired regarding the effectiveness of blood pressure lowering medication over one or more dose-to-dose intervals and/or where doubt exists as to the reliability of ambulatory blood pressure measurement.

In general, blood pressure measurements from relatively large and bulky oscillimetry cuffs (e.g., 5 cm or more in width) have minimal error in the blood pressure measurement. While such blood pressure measurement devices may be adequate for special cases, more convenient blood pressure monitoring may be desirable. More convenient blood pressure monitoring may increase the adoption of non-clinical measurements and monitoring of blood pressure by common consumers, thereby decreasing risks associated with delayed detection of hypertension.

SUMMARY OF THE DISCLOSURE

The present disclosure provides non-invasive devices and methods for determining an pressure of blood within a cardiovascular system of a user. It may be desirable to reduce a bulkiness of current blood pressure measurement devices to make blood pressure measurements more convenient. While reducing the bulkiness of current blood pressure measurement devices may be desirable, doing so may come with additional challenges. For example, blood pressure measurement errors tend to increase as the cuff width decreases (e.g., becomes more narrow). For at least this reason, most blood pressure cuffs on the market are at least 5 cm in width and many blood pressure measurement device manufactures and designers have actually avoided narrowing blood pressure cuff widths further. Blood pressure measurements from wrist-worn devices with narrower bands tend to include measurement errors and blood pressure measurements may be inconsistent from user to user. The errors and inconsistencies may also be due in part to variations in physical characteristics of users (e.g., anatomical variations). Thus, embodiments of the present disclosure may reduce these errors and variability using one or more correction factors. The one or more correction factors may be used to calculate or adjust blood pressure values to provide more accurate blood pressure measurements. In particular, the one or more correction factors may be based on one or more of the following: wrist circumference, target artery depth, and/or tissue density or hydration. The correction factors may allow for more compact (e.g., narrow band widths), convenient, and/or accurate wrist-worn blood pressure measurement devices.

In some embodiments, a wrist-worn device may be provided. The device may include a device housing and one or more bands coupled with the device housing. The one or more bands may be configured to wrap around a portion of a wrist of a user to couple the device housing to the wrist of the user. The one or more bands may be configured to couple with the wrist of the user using one of a plurality of band configurations which accommodate various wrist sizes. A processor may be provided which may be configured to detect the band configuration utilized for coupling the device housing to the wrist of the user using one or more sensors. A pressure sensor may be coupled with the one or more bands. The pressure sensor may be configured to measure pressure signals. The processor may be coupled with the pressure sensor. The processor may be configured to calculate a blood pressure value using the pressure signals from the pressure sensor and a correction factor based on the band configuration detected by the processor (or otherwise adjust a measured blood pressure of the user with the correction factor based on the band configuration detected by the processor).

In some embodiments, the wrist-worn device may have bands with a width less than 5 cm (e.g., less than 3 cm in further embodiments). The one or more bands may include a first band and a second band configured to couple with the first band to couple the device housing to the wrist of the user. The first band may include a plurality of notches and the second band may include a latch configured to couple with one of the plurality of notches of the first band. The band processor may be configured to detect which notch out of the plurality of notches is coupled with the latch in order to determine the band configuration utilized for coupling the device housing to the wrist of the user. The processor may detect a completed circuit formed between the latch and the notch the latch is coupled with in order to determine the band configuration utilized for coupling the device housing to the wrist of the user. In some embodiments, the plurality of notches may each include a metal ring or contact for forming part of the circuit with the latch.

In some embodiments, the latch may interrupt an optical signal at the notch that the latch is coupled with. The processor may detect the interruption of the optical signal at the notch the latch is coupled to in order to determine the band configuration utilized for coupling the device housing to the wrist of the user.

Optionally, the latch may include a magnetic material. The notches may include magnetic sensors. The processor may detect the magnetic material of the latch coupled with one of the plurality of notches via the magnetic sensors in order to determine the band configuration utilized for coupling the device housing to the wrist of the user.

In some embodiments, the one or more bands may include a single band having a first end and a second end opposite the first end. The first end of the band may be coupled with a first side of the device housing and the second end of the band may be configured to be fed through a band loop on a second side of the device housing. The processor may be configured to determine a length of band fed through the band loop in order to determine the band configuration utilized for coupling the device housing to the wrist of the user. The band may be configured to fold back on itself after being fed through the band loop with the second end of the band configured to couple with a portion of the band. The processor may be configured to detect a location of the second end of the band along a length of the band in order to determine the band configuration utilized for coupling the device housing to the wrist of the user. The second end of the band may be configured to couple with the portion of the band via magnetic attraction. The band may include a plurality of magnetic sensors disposed along the length of the band for detecting the location of the second end of the band along the length of the band.

The wrist-worn device may further include an ultrasound transducer configured to determine a depth of a target artery. The processor may be coupled with the ultrasound transducer and may be configured to factor in the depth of the target artery when calculating the blood pressure value. For example, the processor may calculate the blood pressure value using the pressure signals from the pressure sensor, the correction factor based on the detected band configuration, and another correction factor based on the depth of the target artery. Optionally, the processor may calculate the blood pressure value using the pressure signals from the pressure sensor and a correction factor based on the detected band configuration and the depth of the target artery.

In some embodiments, the pressure sensor may be configured to measure the pressure signals from a target artery. The wrist-worn device may further include an actuator coupled with the pressure sensor. The actuator may be configured to be urged against the wrist of the user during pressure measurement by the pressure sensor. The processor may be configured to estimate a depth of the target artery based on the pressure signal from the pressure sensor and an actuation amount (e.g., actuation distance, inflation volume, or the like) by the actuator. The processor may be further configured to factor in the estimated depth of the target artery when calculating the blood pressure value (e.g., calculate or adjust the blood pressure value with another correction factor based on the estimated depth of the target artery).

In some embodiments, the actuator may be a linear actuator. Optionally, the actuator may be a fluid bladder (e.g., an air bladder or the like). In some embodiments, the pressure sensor may be coupled with an interior of the fluid bladder. In some embodiments, the pressure sensor may be coupled with an exterior of the fluid bladder. The fluid bladder may include an optical or ultrasound distance sensor for determining the amount of actuation by the fluid bladder. In further embodiments, the fluid bladder may include a magnet and a magnet sensor for determining the amount of actuation by the fluid bladder. In some embodiments, the actuation amount of the fluid bladder may be determined by a volume of fluid delivered into the fluid bladder.

The pressure sensor may configured to measure the pressure signal from a target artery and the wrist-worn device may include an actuator coupled with the pressure sensor. The actuator may be configured to be urged a distance against the wrist of the user during pressure measurement by the pressure sensor. The processor may be configured to estimate a tissue density based on signals from the pressure sensor and the distance the actuator is urged against the wrist of the user. In some embodiments, the processor may be configured to estimate the tissue density (or tissue hydration) by calculating a derivative of the pressure measured by the pressure sensor with respect to the distance the actuator is displaced against the wrist of the user (dP/dZ). The processor may be configured to factor in the estimated tissue density when calculating the blood pressure value (e.g., calculate or adjust the blood pressure value with another correction factor based the estimated tissue density).

In further embodiments of the present disclosure, a wrist-worn device may be provided that includes a pressure sensor configured to measure a pressure signal from a target artery. An ultrasound transducer may be provided that is configured to determine a depth of the target artery. A processor may be coupled with the pressure sensor. The processor may be configured to calculate a blood pressure value using the pressure signal from the pressure sensor and a correction factor based on the determined depth of the target artery or otherwise adjust a blood pressure value with a correction factor based on the depth of the target artery.

In still further embodiments, a wrist-worn device may be provided that includes a pressure sensor configured to measure pressure signals from a target artery. An actuator may be coupled with the pressure sensor. The actuator may be configured to be urged against the wrist of the user during pressure measurement by the pressure sensor. A processor may be coupled with the pressure sensor and the actuator. The processor may be configured to estimate a depth of the target artery based on the pressure signal from the pressure sensor and an actuation amount by the actuator. The processor may be further configured to factor in the estimated depth of the target artery when calculating the blood pressure value (e.g., calculate or adjust the blood pressure value with a correction factor based on the estimated depth of the target artery).

The pressure sensor may be configured to measure a pressure at a contact end of the actuator. The processor may estimate the depth of the target artery by: identifying initial contact of the contact end of the actuator with the wrist of the user as the actuator is urged against the wrist of the user using pressure signals from the pressure sensor, identifying a mean arterial pressure measured by the pressure sensor; and identifying a distance actuated by the actuator from the initial contact of the contact end of the actuator and a position of the contact end of the actuator when identifying the mean arterial pressure.

The actuator may be a linear actuator. Optionally, the actuator may be a fluid bladder configured to urge a contact end of the fluid bladder in a distal direction from a proximal end of the fluid bladder. The pressure sensor may be coupled with an interior of the fluid bladder. In some embodiments, the pressure sensor may be coupled with an exterior of the fluid bladder. The fluid bladder may include an optical or ultrasound distance sensor for determining the amount of actuation by the fluid bladder. The optical or ultrasound distance sensor may be positioned at the proximal end of the fluid bladder and may reflect energy (e.g., electromagnetic or sound) off of the contact end of the fluid bladder in order to determine the amount of actuation by the fluid bladder.

The fluid bladder may include a magnet and a magnet sensor for determining the amount of actuation by the fluid bladder. Optionally, the actuation amount of the fluid bladder may be determined by a volume of fluid delivered into the fluid bladder.

The processor may be configured to estimate a tissue density based on signals from the pressure sensor and the distance the actuator is urged against the wrist of the user. The processor may be configured to estimate the tissue density by calculating a derivative of the pressure measured by the pressure sensor with respect to the distance the actuator is urged against the wrist of the user. In some embodiments, the processor may be configured to calculate or adjust the blood pressure value with a correction factor based the estimated tissue density.

In still further embodiments of the present disclosure, a wrist-worn device may be provided. The wrist-worn device may include a pressure sensor configured to measure blood pressure signals from a target artery. An actuator may be coupled with the pressure sensor. The actuator may be configured to be urged against the wrist of the user by a distance during pressure measurement by the pressure sensor. A processor may be coupled with the pressure sensor and the actuator. The processor may be configured to estimate a tissue density based on signals from the pressure sensor and the distance the actuator is urged against the wrist of the user and to calculate a blood pressure value using the pressure signals from the pressure sensor and a correction factor based on the estimated tissue density. The processor may be configured to estimate the tissue density by calculating a derivative of the pressure measured by the pressure sensor with respect to the distance the actuator is urged against the wrist of the user.

In some embodiments of the present disclosure, a method of measuring a blood pressure of a user may be provided. The method may use a device having a device housing and one or more bands coupled with the device housing and configured to wrap around a portion of a wrist of the user to couple the device housing to the wrist of the user. The one or more bands may be configured to couple with the wrist of the user using one of a plurality of band configurations which accommodate various wrist sizes. The method may include measuring a pressure signal from the user using a pressure sensor coupled with the one or more bands of the device. The band configuration utilized for coupling the device housing to the wrist of the user may be detected with a processor. The processor may then calculate a blood pressure value with the pressure signal from the pressure sensor and a correction factor based on the band configuration detected by the processor. The blood pressure value may then be outputted.

The one or more bands may include a first band and a second band configured to couple with the first band to couple the device housing to the wrist of the user. The first band may include a plurality of notches and the second band may include a latch configured to couple with one of the plurality of notches of the first band. The band configuration may be detected with the processor by detecting which notch out of the plurality of notches is coupled with the latch. In some embodiments, the band configuration may be detected with the processor by detecting a completed circuit formed between the latch and the notch the latch is coupled with.

Optionally, detecting the band configuration with the processor includes detecting an interruption of an optical signal by the latch at the notch that the latch is coupled with. In some embodiments, detecting the band configuration with the processor includes detecting a magnetic material of the latch coupled with one of the plurality of notches via magnetic sensors associated with each of the notches.

In some embodiments, the one or more bands may include a single band having a first end and a second end opposite the first end. The first end of the band may be coupled with a first side of the device housing and the second end of the band may be configured to be fed through a band loop on a second side of the device housing. Detecting the band configuration with the processor may include determining a length of band fed through the band loop. In some situations, the band may be configured to fold back on itself after being fed through the band loop with the second end of the band configured to couple with a portion of the band. Detecting the band configuration with the processor may include detecting a location of the second end of the band along a length of the band.

In some embodiments a depth of a target artery may be determined using an ultrasound transducer. The depth of the target artery may be factored in when calculating the blood pressure value (e.g., calculating the blood pressure value with a correction factor based on the depth of the target artery or where the correction factor is a function of the depth of the target artery). The wrist-worn device may further include an actuator coupled with the pressure sensor. The actuator may be configured to be urged against the wrist of the user during pressure measurement by the pressure sensor. The method may further include estimating a depth of a target artery based on a pressure signal from the pressure sensor and an actuation amount by the actuator. In some embodiments, the method may include calculating or adjusting the blood pressure value with another correction factor based on the estimated depth of the target artery or otherwise factoring the estimated depth of the target artery into the blood pressure value calculation. The actuator may include a fluid bladder that includes an optical or ultrasound distance sensor. The method may further include determining the amount of actuation by the fluid bladder by reflecting energy off a distal contact end of the fluid bladder from a proximal end of the fluid bladder.

The actuator may be a fluid bladder that includes a magnet and a magnet sensor. Determining the amount of actuation by the fluid bladder may include measuring a change in magnetic force during actuation. The actuator may be a fluid bladder and the method may include determining the actuation amount of the fluid bladder by measuring a volume of fluid delivered into the fluid bladder.

In some embodiments, pressure sensor may be configured to measure the pressure from a target artery. The wrist-worn device may further comprise an actuator coupled with the pressure sensor. The actuator may be configured to be urged a distance against the wrist of the user during blood pressure measurement by the pressure sensor. The method may further include estimating a tissue density based on signals from the pressure sensor and the distance the actuator is urged against the wrist of the user. In some embodiments, estimating the tissue density may include calculating a derivative of the pressure measured by the pressure sensor with respect to the distance the actuator is urged against the wrist of the user. The method may further include calculating a blood pressure value using the pressure signal from the pressure sensor and a correction factor based the estimated tissue density or otherwise factoring the estimated tissue density into the blood pressure value calculation.

In further aspects of the present disclosure, a method may be provided that includes measuring a pressure signal of the user from a target artery using a pressure sensor and determining a depth of the target artery using an ultrasound transducer. A blood pressure value may then be calculated using the measured pressure from the pressure sensor and a correction factor based on the depth of the target artery. The blood pressure value may be outputted (e.g., to the user or to another device for later access by the user or a physician or the like).

In additional embodiments, a method may be provided that includes measuring a pressure from a target artery using a pressure sensor and urging an actuator coupled with the pressure sensor against the wrist of the user during blood pressure measurement by the pressure sensor. A depth of the target artery may be estimated based on a pressure signal from the pressure sensor and an actuation amount by the actuator. A blood pressure value may be calculated or adjusted with a correction factor based on the estimated depth of the target artery. The blood pressure value may be outputted to the user or the like.

Estimating the depth of the target artery may include identifying an initial contact of a contact end of the actuator with the wrist of the user as the actuator is urged against the wrist of the user using pressure signals from the pressure sensor, identifying a mean arterial pressure measured by the pressure sensor, and identifying a distance actuated by the actuator from the initial contact of the contact end of the actuator and a position of the contact end of the actuator when identifying the mean arterial pressure.

The actuator may include a fluid bladder. The bladder may have an optical or ultrasound distance sensor. The method may further include determining the amount of actuation by the fluid bladder by reflecting energy off a distal contact end of the fluid bladder from a proximal end of the fluid bladder.

The actuator may be a fluid bladder that includes a magnet and a magnet sensor. Determining the amount of actuation by the fluid bladder may be performed by measuring a change in magnetic force during actuation. Optionally, the actuation amount of the fluid bladder may be determined by measuring a volume of fluid delivered into the fluid bladder.

The method may further include estimating a tissue density associated with the wrist based on signals from the pressure sensor and a distance the actuator is urged against the wrist of the user. The tissue density may be estimated by calculating a derivative of the pressure measured by the pressure sensor with respect to the distance the actuator is urged against the wrist of the user. The blood pressure value of the user may be calculated or adjusted with a correction factor based the estimated tissue density.

In further embodiments of the present disclosure, a method of measuring and/or adjusting blood pressure measurement may be provided. The method may include measuring a the pressure signal from a target artery using a pressure sensor. An actuator coupled with the pressure sensor may be urged against the wrist of the user by a distance during pressure measurement by the pressure sensor. A tissue density may be estimated based on signals from the pressure sensor and the distance the actuator is urged against the wrist of the user. The blood pressure value may be calculated with the pressure signals from the pressure sensor and a correction factor based on the estimated tissue density. The calculated blood pressure measurement may then be outputted to the user or the like.

The tissue density may be estimated by calculating a derivative of the pressure measured by the pressure sensor with respect to the distance the actuator is urged against the wrist of the user.

Embodiments of the disclosure covered by this patent are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The disclosure will be better understood on reading the following description and examining the figures that accompany it. These figures are provided by way of illustration only and are in no way limiting on the disclosure.

DETAILED DESCRIPTION

The present disclosure generally relates to blood pressure monitoring. In some embodiments, methods and devices for measuring a mean arterial pressure and/or for monitoring blood pressure changes of a user are provided. Pressure signals measured by one or more pressure sensors may be adjusted using one or more correction factors to calculate a blood pressure value associated with a user as will be described further below. The use of the one or more correction factors disclosed herein may allow more compact, convenient, and/or accurate wearable blood pressure measurement devices and methods. In particular, wrist-worn devices may be provided which are less bulky than current devices and account for anatomical variations so as to facilitate more frequent and accurate blood pressure monitoring.

Figure 1:
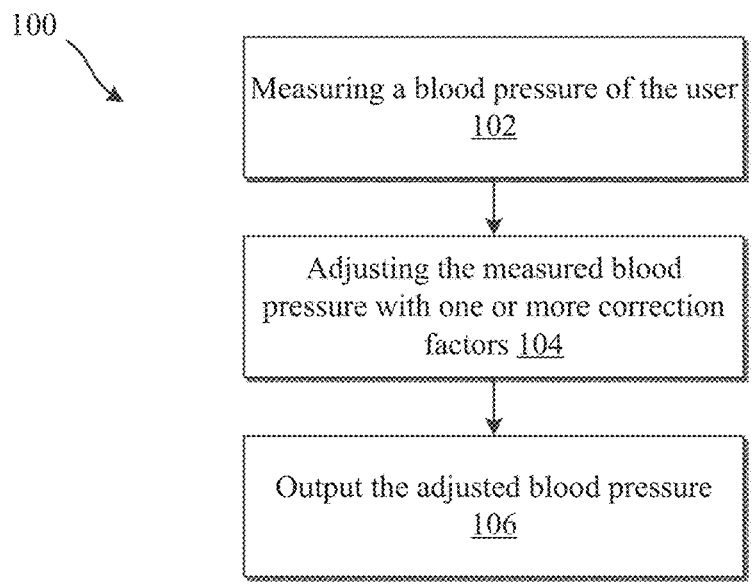
FIG. 1 shows an exemplary method according to some embodiments of the present disclosure.

FIG. 1 shows an exemplary method 100 according to some embodiments of the present disclosure. Method 100 may start with a measurement of a blood pressure of a user 102. Thereafter, the measured blood pressure may be adjusted using one or more correction factors 104. The adjusted blood pressure may then be outputted 106 (e.g., to user or the like).

In some embodiments, the user's blood pressure may be measured 102 using a wrist-worn device. For example, in some embodiments, the wrist-worn device may have bands that are less than 5 cm in width. In some embodiments, it may be preferable to measure blood pressure 102 using a wrist-worn device having bands less than 3 cm in width (e.g., 2.5 cm or less). The wrist-worn device may measure blood 102 using applanation tonometry or oscillometry according to some embodiments.

In applanation tonometry, the pressure in a superficial artery with sufficient bony support, such as the radial artery, may be accurately recorded during an applanation sweep when the transmural pressure equals zero. An applanation sweep refers to a time period during which pressure over the artery is varied from overcompression to undercompression or vice versa. At the onset of a decreasing applanation sweep, the artery is overcompressed into an occluded state, so that pressure pulses are not recorded. At the end of the sweep, the artery is undercompressed, so that minimum amplitude pressure pulses are recorded. Within the sweep, it is assumed that an applanation occurs where the arterial wall is flattened and transmural pressure turns to zero, and the arterial pressure is perpendicular to the surface and is the only pressure detected by a tonometer sensor.

Figure 2:
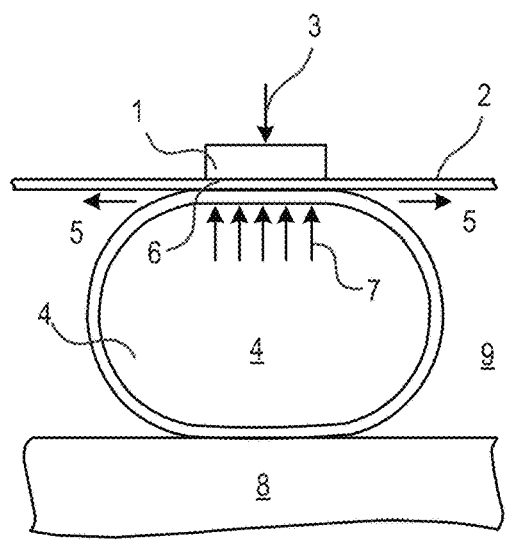
FIG. 2 illustrates a method of applanation tonometry that may be used with embodiments of the methods and devices of the present disclosure.
Figure 3:
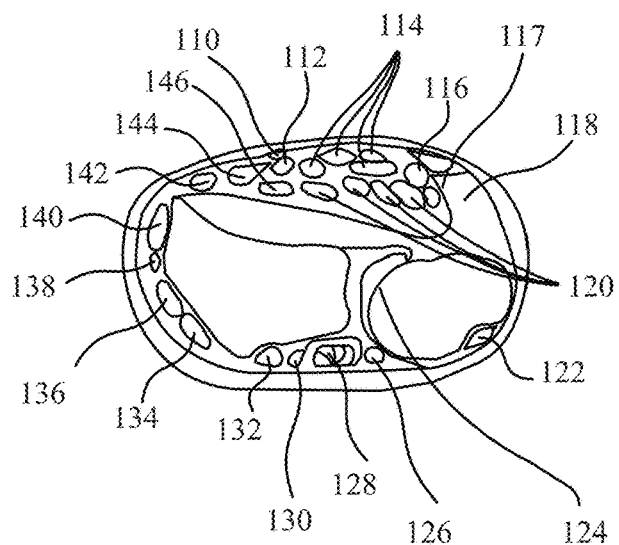
FIG. 3 shows the cross section of a wrist.

FIG. 2 illustrates a method of applanation tonometry that may be used with embodiments of the methods and devices of the present disclosure. Here, a pressure transducer 1 is urged against the skin 2 of a user with an applanation force 3. The applanation force 3 and pressure transducer 1 applanate the target artery 4 such that the arterial wall tension 5 is parallel to the pressure transducer surface 6 and the arterial pressure 7 is perpendicular to the surface 6. Where the target artery 4 is applanated in such a manner, the arterial pressure may be measured by transducer 1. The target artery 4 may be supported by bone 8 and adjacent muscle 9. The target artery 4 may be the radial artery of the user and the bone 8 may be the radial bone. FIG. 3 illustrates an exemplary cross-section of a wrist which may include: palmaris longus tendon 110, median nerve 112, flexor dig. sublimis 114, ulnar artery 116, ulnar nerve 117, flexor carp. uln. 118, flex. dig. profundus 120, ext. carp. uln. 122, distal radio-unlar artic. 124, ext. dig. quinti prop. 126, ext. dig. commun. 128, ext. indicis. prop. 130, ext. poll. long. 132, ext. carp. rad. brev. 134, ext. carp. rad. long. 136, ext poll brev. 138, abd. poll. long. 140, radial artery 142, flex. carp. rad. 144, and flex. poll. long. 146. As mentioned above, the radial artery 142 is generally targeted in arterial applanation tonometry given its position adjacent the radial bone (radius).

Figure 4:
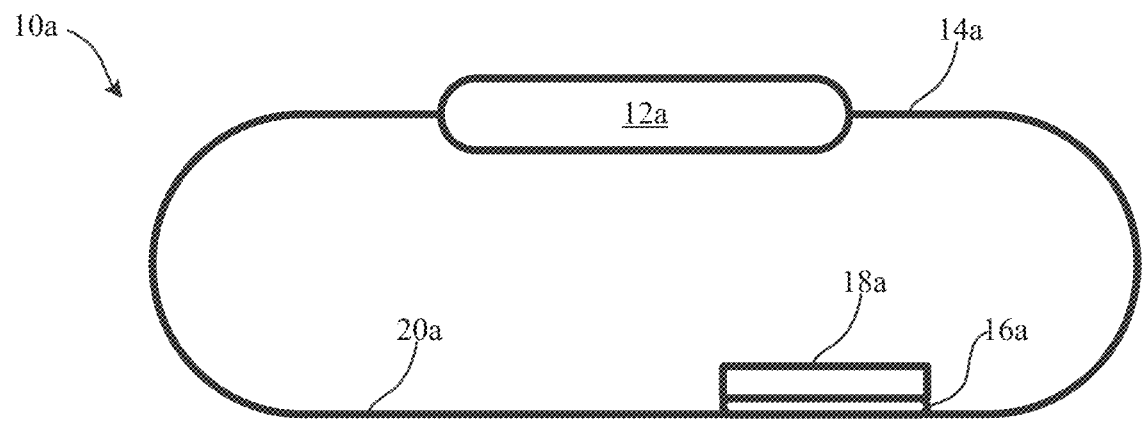
FIG. 4 illustrates the an exemplary device according to some embodiments of the present disclosure.

FIG. 4 illustrates the an exemplary device 10a that may measure blood pressure using applanation tonometry according to some embodiments of the present disclosure. Device 10a may include a device housing/body 12a and a band 14a. An actuator 16a may be supported by device band 14a. A pressure sensor 18a may be coupled with actuator 16a.

In many embodiments, the device 10a may be a wrist-worn device (e.g., an electronic watch or the like). The device body 12a may house a data processor of device 10a. The device body 12a may also provide a user interface for receiving user input and outputting information to the user (e.g., through a display or integrated audio device or the like). In some embodiments, the input may be configured to receive anthropometric data associated with the user (e.g., wrist circumference, BMI, height, weight, age, etc.) that may be used to correct blood pressure measurements. The device band 14a may comprise one or more flexible bands configured to couple the device 10a to the user (e.g., to the user's wrists). Optionally, the device bands 14a includes two bands configured to couple with one another to couple the device 10a to the user. One band may include a plurality of notches and the other band may include a latch configured to couple with one of the plurality of notches. The device body 12a and the device band 14a may have a skin engaging surface 20a. In some embodiments, it may be preferable if the device 10a does not require a harness for positioning the user's wrist in a particular manner when measuring a blood pressure of the user. Avoiding a wrist harness may decrease the bulkiness of the device 10a and may increase the adoption of device 10a for blood pressure measurements by general consumers.

The actuator 16a may be a linear actuator for driving the sensor 18a into the skin of the user. For example, the actuator 16a may urge the sensor 18a against a target artery of the user to conduct an applanation sweep for applanation tonometry. The actuator 16a may be a fluid bladder or the like. In some embodiments actuator 16a may be an array of actuators. For example, an array of actuators may selectively urge different portions of the sensor 18a against a skin of the user. Such selective urging may be performed for identifying certain portions of the sensor 18a that may be better positioned for measuring a blood pressure from a target artery.

The sensor 18a may be a single pressure sensor in some embodiments. In further embodiments, the sensor 18a may be an array of pressure sensors. In some embodiments, the array of pressure sensors may be an array of capacitive pressure sensors. In some embodiments, the array of pressure sensors may be an array of piezoresistive pressure sensors.

The sensor 18a may be coupled with the data processor housed in device body 12a or may be operatively coupled with a separate processor that is coupled with the device band 14a. Alternatively, there may be control/processing circuitry in the band 14a, but the processor of the device body 12a may be used for signal processing.

In further embodiments, blood pressure may be measured using oscillometry. Typically, in oscillometry blood pressure measurement, an inflatable cuff or bladder is applied around an extremity of a user, such as the wrist. The cuff may then be inflated to a pressure above the user's systolic pressure and then incrementally reduced in a series of small steps. A pressure sensor pneumatically connected to the cuff may measure the cuff pressure throughout the deflation process. The pressure sensor may measure the pressure fluctuations occurring within the cuff due to blood flowing through the user's arteries. With each beat, blood flow causes small changes in the artery volume which are transferred to the inflated cuff, further causing slight pressure variations within the cuff which are then detected by the pressure sensor. The pressure sensor may produce an electrical signal representing the cuff pressure level combined with a series of small periodic pressure variations associated with the beats of a user's heart for each pressure step during the deflation process. As the cuff pressure is decreased, the oscillation size begins to grow and eventually reaches a maximum amplitude. After the oscillation size reaches the maximum amplitude, the oscillation size decreases as the cuff pressure continues to decrease. Physiologically, the cuff pressure at the maximum oscillation amplitude value approximates the mean arterial. In addition, complex amplitudes at cuff pressures equivalent to the systolic and diastolic pressures may have a fixed relationship to this maximum oscillation amplitude value. Thus, the oscillometric method may be based upon measurements of detected oscillation amplitudes at various cuff pressures.

Blood pressure measuring devices operating according to the oscillometric method detect the amplitude of the pressure oscillations at various applied cuff pressure levels. The amplitudes of these oscillations, as well as the applied cuff pressure, may be stored together as the device automatically changes the cuff pressures through a predetermined pressure pattern. These oscillation amplitudes define an oscillometric "envelope" and may be evaluated to find the maximum value and its related cuff pressure, which is approximately equal to MAP. The cuff pressure below the MAP value which produces an oscillation amplitude having a certain fixed relationship to the maximum value may be designated as the diastolic pressure, and, likewise, the cuff pressures above the MAP value which results in complexes having an amplitude with a certain fixed relationship to that maximum value may be designated as the systolic pressure. The relationships of oscillation amplitude at systolic and diastolic pressures, respectively, to the maximum value at MAP may be empirically derived ratios depending on the preferences of those of ordinary skill in the art. Generally, these ratios are designated in the range of 40%-80% of the amplitude at MAP.

Figure 5:
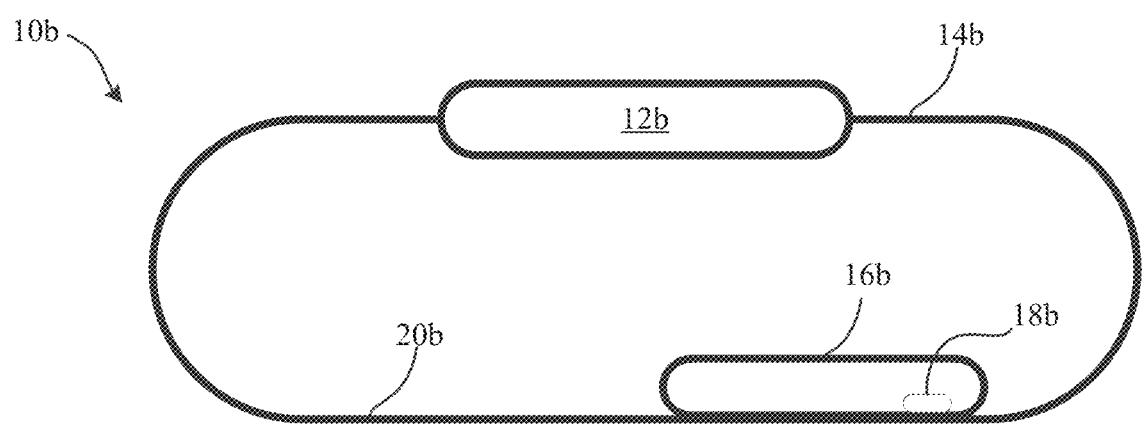
FIG. 5 illustrates another exemplary device according to some embodiments of the present disclosure.

FIG. 5 illustrates another exemplary device 10b that may measure blood pressure using oscillometry according to some embodiments of the present disclosure. Device 10b may include a device housing/body 12b and a band 14b. An actuator 16b may be supported by device band 14b. A pressure sensor 18b may be coupled with actuator 16b.

In many embodiments, the device 10b may be a wrist-worn device (e.g., an electronic watch or the like). The device body 12b may house a data processor of device 10b. The device body 12b may also provide a user interface for receiving user input and outputting information to the user (e.g., through a display or integrated audio device or the like). The device band 14b may comprise one or more flexible bands configured to couple the device 10b to the user (e.g., to the user's wrists). Optionally, the device bands 14b includes two bands configured to couple with one another to couple the device 10b to the user. One band may include a plurality of notches and the other band may include a latch configured to couple with one of the plurality of notches. The device body 12b and the device band 14b may have a skin engaging surface 20b. In some embodiments, it may be preferable if the device 10b does not require a harness for positioning the user's wrist in a particular manner when measuring a blood pressure of the user. Avoiding a wrist harness may decrease the bulkiness of the device 10b and may increase the adoption of device 10b for blood pressure measurements by general consumers.

The actuator 16b may be a cuff/fluid bladder that may be inflated to occlude a target artery and then incrementally reduced for measuring a blood pressure using oscillometry.

The sensor 18b may be a pressure sensor in some embodiments. The pressure sensor may be dispose in an interior of the actuator/cuff 16b and may be configured to measure the cuff pressure throughout the deflation process. The pressure sensor may measure the pressure fluctuations occurring within the cuff due to blood flowing through the user's arteries and send the signals to a processor for further processing.

The sensor 18b may be coupled with the data processor housed in device body 12b or may be operatively coupled with a separate processor that is coupled with the device band 14b. Alternatively, there may be control/processing circuitry in the band 14b, but the processor of the device body 12b may be used for signal processing.

Figure 6:
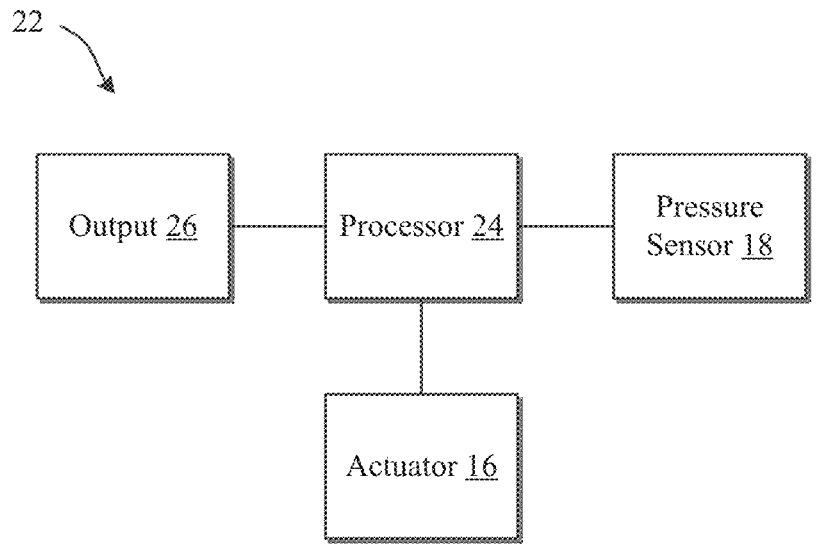
FIG. 6 illustrates an exemplary system according to some embodiments of the present disclosure.

FIG. 6 illustrates an exemplary system diagram 22 of device 10a or 10b according to some embodiments of the present disclosure. The device 10a, 10b may include a processor 24. The processor 24 may be coupled with and may control actuation of the actuator 16a, 16b. Additionally, the processor 24 may be further coupled with the sensor 18a, 18b. The processor 24 may be configured to receive signals from the sensor 18a, 18b and may be further configured to process the signals to determine a pressure sensed by the sensor 18a, 18b. The processor 24 may detect and compute a pulse rate of the user and/or a blood pressure measurement of the user based on the one or more signals from the sensors 18a, 18b. The processor 24 may then output the measured attribute to the user in a manner perceptible to the user via output 26. The output 26, may be an audio output, a display, or the like. In some embodiments, the data may be wirelessly communicated to another electronic device associated with the user for further processing or output to the user or a physician or the like. As set forth above, processor 24 may be housed in the device body 12a, 12b or may be coupled with the device band 14a, 14b.

Additionally, as described above, the processor 24 may be configured to calculate a blood pressure value using one or more correction factors or otherwise adjust a measured blood pressure using one or more correction factors to provide a more accurate blood pressure measurement. This may be particularly desirable when measuring blood pressure using a wrist-worn device having narrow band widths. As set forth above, in general, blood pressure measurements from relatively large and bulky oscillimetry cuffs (e.g., 5 cm or more in width) have minimal error in the blood pressure measurement. While such blood measurement devices may be adequate for special cases, it may be desirable to reduce a bulkiness of blood measurement devices to provide more convenient blood pressure monitoring. For example, in some situations, it may be desirable to be able to measure blood pressure from a wrist-worn device (such as an electronic watch or the like). The more convenient blood pressure monitoring may increase the adoption of non-clinical measurements and monitoring of blood pressure by common consumers. This may encourage more frequent blood pressure measurements by users (e.g., daily, weekly, monthly, or the like), thereby increasing the likelihood of detecting hypertension and decreasing risks associated with delayed detection of hypertension.

Reducing the bulkiness of current blood pressure measurement devices may be desirable, but doing so comes with additional challenges. Blood pressure measurement errors tend to increase as the cuff width decreases (e.g., becomes more narrow). For at least this reason, most blood pressure cuffs on the market are at least 5 cm in width and many blood pressure measurement device manufactures and designers have actually avoided narrowing blood pressure cuff widths further. Blood pressure measurements from wrist-worn devices with narrower bands tend to include measurement errors and blood pressure measurements may be inconsistent from user to user. The errors and inconsistencies may be due in part to variations in physical characteristics of users. Thus, embodiments of the present disclosure may reduce these errors and variability using one or more correction factors.

At least some of the errors may be related to a target artery depth and/or a tissue density of the user. For example, blood pressure measurement errors may increase with an increase in target artery depth. Deeper target arteries may require wider cuffs that can apply applanation or occlusion pressure down to those depths with less variation between the pressure applied at the surface of the skin of the user and the pressure experienced at the target artery. With narrower cuffs, the pressure experienced at the target artery may actually be some fraction of the pressure applied at the surface of the skin (e.g., in a tonometry or oscillometry approach), because a portion of the applied pressure at the surface of the skin may become more dispersed at greater tissue depths. Thus the applanation force (in applanation tonometry) or cuff pressure (in oscillometry) measured may vary from the pressure actually acting at a deep target artery. This difference in applied pressure and pressure experienced at the target artery may be responsible in part for some of the errors in blood pressure measurement. Additionally, the amount of dispersion of the applied pressure within the tissue may be correlated to a composition or a hydration of the tissue disposed between the actuator and the target artery. In some embodiments, a tissue density may be estimated and a correction factor may be applied to a measured blood pressure to account for the variation in tissue composition and/or hydration between user to user. Accordingly, the processor 24 may be coupled with additional sensors that are configured to measure physiological parameters of the user that are associated with one or more of the correction factors. For example, as will be described further below, the processor 24 may be coupled with ultrasound sensors, optical sensors, magnetic sensors (e.g., hall effect sensors or the like), electronic circuit sensors, or the like to estimate physiological parameters that may be associated with sources of error in blood pressure measurements. Correction factors may then be used when calculating blood pressure values in order to account for these sources of error.

Figure 7:
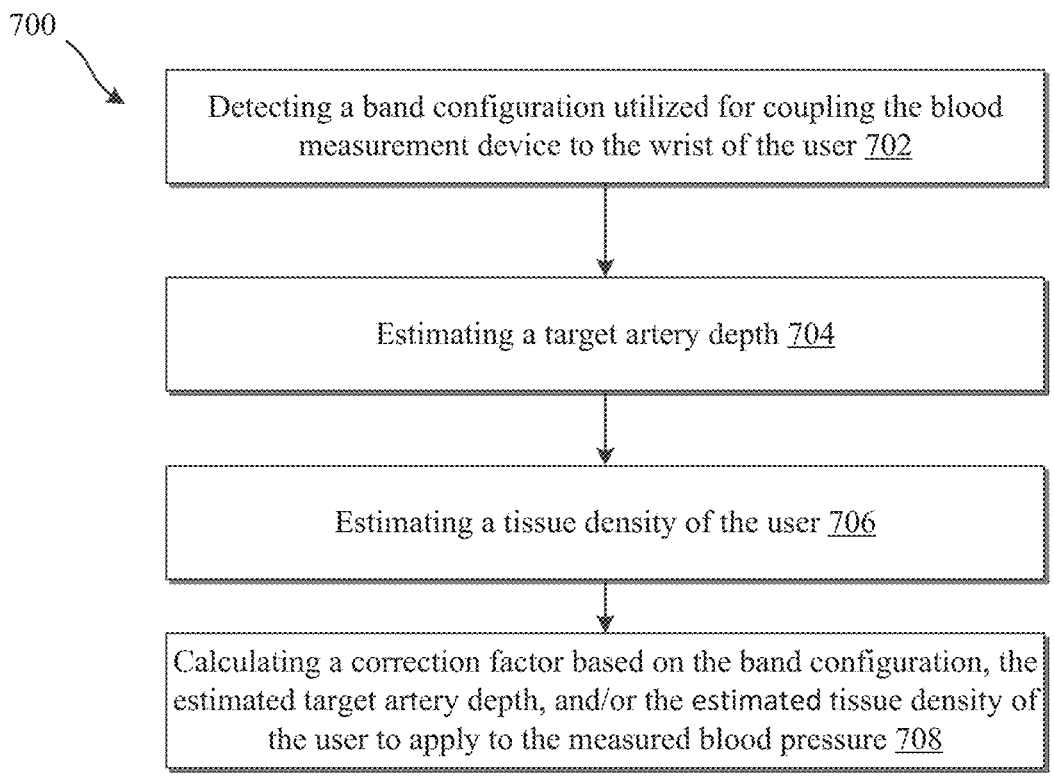
FIG. 7 illustrates an exemplary method of determining a correction factor for application to a measured blood pressure according to some embodiments.

FIG. 7 illustrates an exemplary method 700 of determining a correction factor for application to a measured blood pressure or for use when calculating a blood pressure value associated with a user according to some embodiments. At 702, a band configuration may be detected that is utilized for coupling the blood measurement device to the wrist of the user. At 704, a target artery depth may be estimated. At 706, a tissue density of the user may be estimated. At 708, one or more correction factors for application to the measured blood pressure may be calculated based on the band configuration, the estimated target artery depth, and/or the estimated tissue density of the user.

As set forth above, a band configuration may be detected 702 and a correction factor may be based on the detected band configuration. For example, a band configuration utilized for coupling the wrist-worn device to a user may be associated with a wrist circumference of a user and a correction factor may be based on the band configuration/estimated wrist circumference. The wrist circumference may be associated with a target artery depth of the user. For example, typically, a target artery may be deeper in users with larger wrist circumferences. In some embodiments, anthropometric data may be used to associate a band configuration/estimated wrist circumference to a target artery depth of the user. Thereafter a correction factor may be applied to the measured blood pressure or otherwise factored into a blood pressure value calculation. With deeper target arteries, the actual blood pressure may be a fraction of the measured pressure at the skin surface. With shallow target arteries, the actual blood pressure may closely correspond with the measured pressure at the skin surface. Thus, small or no correction factor may be needed when target arteries are shallow or when a band configuration/estimated wrist circumference is small or below a threshold size. Larger band configurations/estimated wrist circumferences or deeper target arteries may be associated with larger correction factors. For example, in some extreme cases, the actual blood pressure of a user with a deep target artery (e.g., radial artery or the like) may be up to 5% less than a pressure applied and measured at the wrist of the user, and in some cases even up to 10% less than a pressure applied and measured at the wrist of the user due to dispersion of the applied pressure in the tissue disposed between the skin surface and the target artery.

Figure 8:
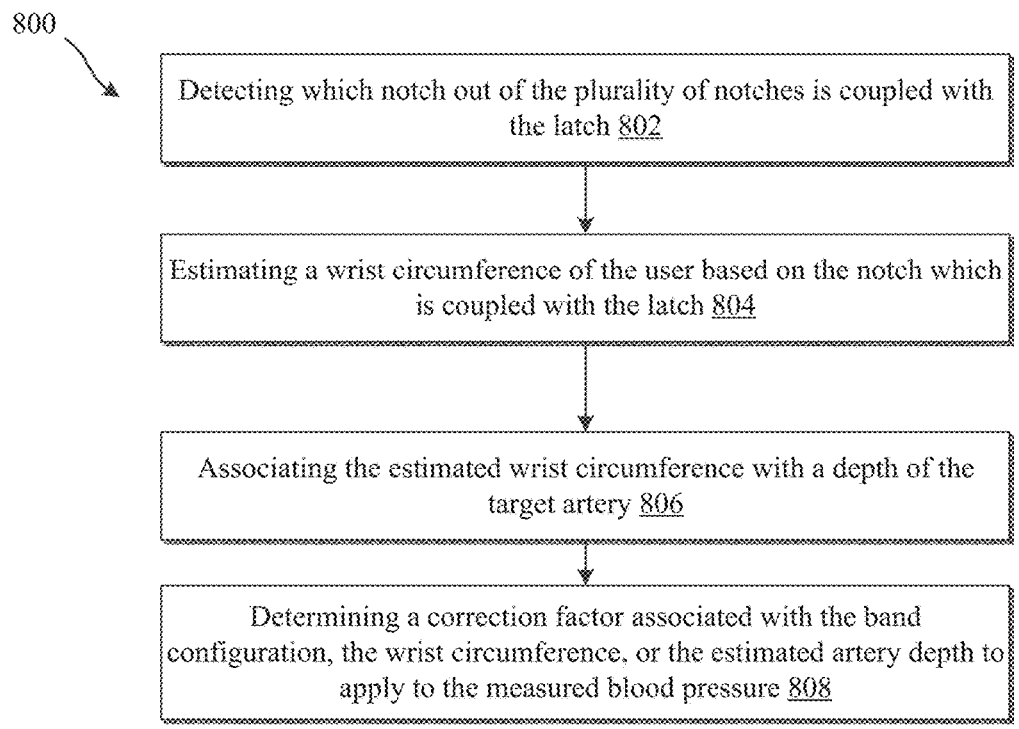
FIG. 8 illustrates an exemplary method of determining a correction factor associated with a band configuration/estimated wrist circumference, and/or an estimated target artery depth to apply to a measured blood pressure according to some embodiments.

FIG. 8 illustrates an exemplary method 800 of determining a correction factor associated with a band configuration/estimated wrist circumference, and/or an estimated target artery depth to apply to a measured blood pressure according to some embodiments. The method 800 may be applicable with device embodiments where the device includes at least two bands which couple with one another to attach the device to a wrist of the user. One band may include a plurality of notches and the other band may include a latch configured to couple with one of the plurality of notches to fasten the device to the wrist of the user. The method 800 may start by detecting 802 which notch out of the plurality of notches on a first band is coupled with the latch of the an opposing band to determine a band configuration or notch setting of the device. A wrist circumference may then be estimated based on the band configuration or notch setting of the device 804. Then, the estimated wrist circumference may be associated with a depth of the target artery 806. A correction factor for application to the measured blood pressure may then be determined 808. The correction factor may be based on the detected band configuration/estimated wrist circumference, and/or the estimated artery depth.

Figure 9:
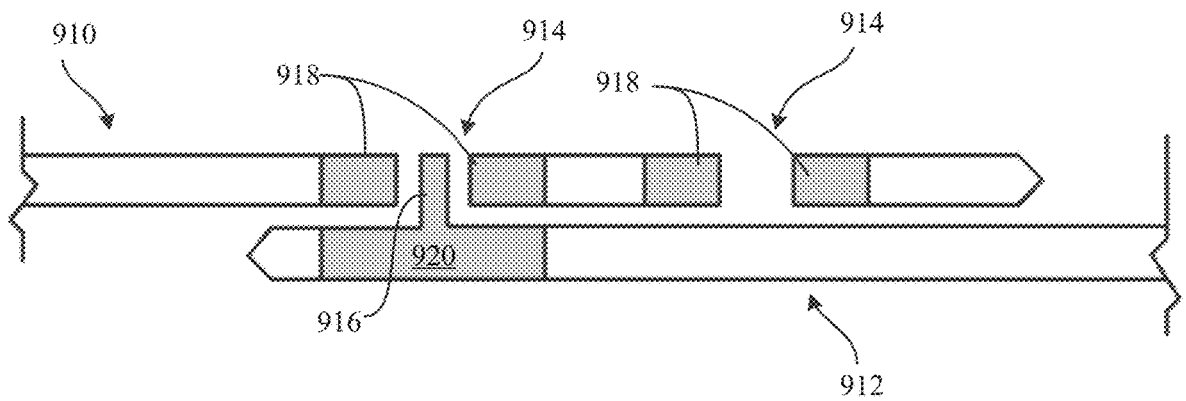
FIG. 9 illustrates exemplary device bands for detecting a band configuration/estimating a wrist circumference, and/or estimating a target artery depth according to embodiments of the present disclosure.

FIG. 9 illustrates exemplary device bands 910, 912 for detecting a band configuration/estimating a wrist circumference, and/or estimating a target artery depth according to embodiments of the present disclosure. As illustrated, the band 910 may include a plurality of notches 914. The band 912 may include a latch 916 which is configured to couple with one of the notches 914 of the band 910 to fasten the device to a wrist of the user. The bands 910, 912 may include sensors for sensing a band configuration utilized to fasten the device to the user. The sensors may include a first component 918 at each of the notches 914 and a second component 920 at the latch 916.

In some embodiments, one of the first components 918 at a notch 914 may complete an electrical circuit with the second component 920 when the latch 916 is coupled with the corresponding notch 914. For example, the first components 918 may be electrically conductive grommets, receptacles or the like. The second component 920 of latch 916 may also be electrically conductive to complete a circuit with a coupled first component 918 at one of the notches 914. In some embodiments, the processor 24 may be configured to detect whether a circuit is completed between the first and second components 918, 920 and which notch 914 is associated with the detected completed circuit.

In further embodiments, optical signals may be formed at each notch 914 by each of the first components 918. In alternative embodiments, first components 918 may be proximity sensors. The latch 916 may be configured to interrupt an optical signal at a coupled notch 914 or may be detected by a proximity sensor at one of the coupled notches 914. The processor 24 may be configured to detect which one of the optical signals are interrupted by the latch 916 or which proximity sensor is triggered by the coupling of the latch 916 to a notch 914 to identify the corresponding notch 914 when the bands 910, 912 are coupled with one another.

In still further embodiments, the first components 918 at a notch 914 may comprise a magnetic sensor (e.g., hall effect sensor or the like) and the second component 920 may be a magnetic material (or vice versa). The processor 24 may be configured to detect which notch 914 the latch 916 is coupled to based on signals from each of the magnetic sensors disposed at the notches 914.

With information on device configuration (e.g., band lengths, device housing length, locations, or the like), a circumference formed by the bands and device housing in the detected band configuration may be calculated. The circumference associated with the detected band configuration may be correlated to the user's wrist circumference. In some embodiments, the band configuration/estimated wrist circumference may then be used to estimate the target artery depth. This may be performed for example, by using look up tables based on anthropometric data. In some embodiments, an algorithm may be provided based on test data that relates a target artery depth to a wrist circumference. Thereafter a correction factor based on the band configuration/estimated wrist circumference and/or the estimated target artery depth may be determined for calculating a blood pressure value or for application to a measured blood pressure of a user to provide for an adjusted, and more accurate, blood pressure measurement 808.

Figure 10:
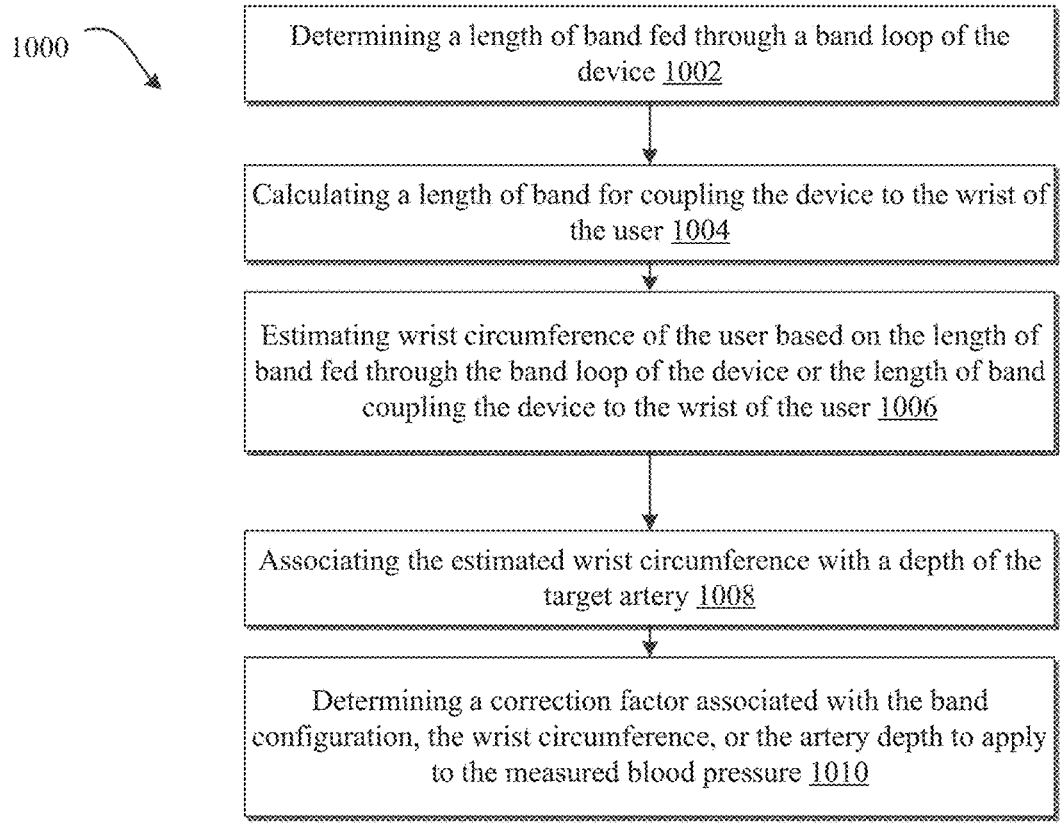
FIG. 10 illustrates another exemplary method for determining a correction factor associated with a band configuration/estimated wrist circumference, and/or an estimated target artery depth to apply to a measured blood pressure according to some embodiments.

FIG. 10 illustrates another exemplary method 1000 for determining a correction factor associated with a band configuration/estimated wrist circumference, and/or an estimated target artery depth to apply to a measured blood pressure according to some embodiments. The method 1000 may be applicable with device embodiments where the device includes a band which couples with a first side of a device housing and where the band is configured to be fed through a band loop disposed on a side opposite the first side of the device housing to couple the device to a user (an example of which is described further below). At 1002, a length of band fed through a band loop of the device may be determined. A length of the and coupling the device to the wrist of the user may then be calculated 1004. A wrist circumference may be estimated based on the length of band fed through the band loop of the device or the length of band coupling the device to the wrist of the user 1006. The estimated wrist circumference may then be associated with a depth of the target artery 1008. A correction factor associated with the band configuration/wrist circumference, or the target artery depth may be determined 1010.

Figure 11:
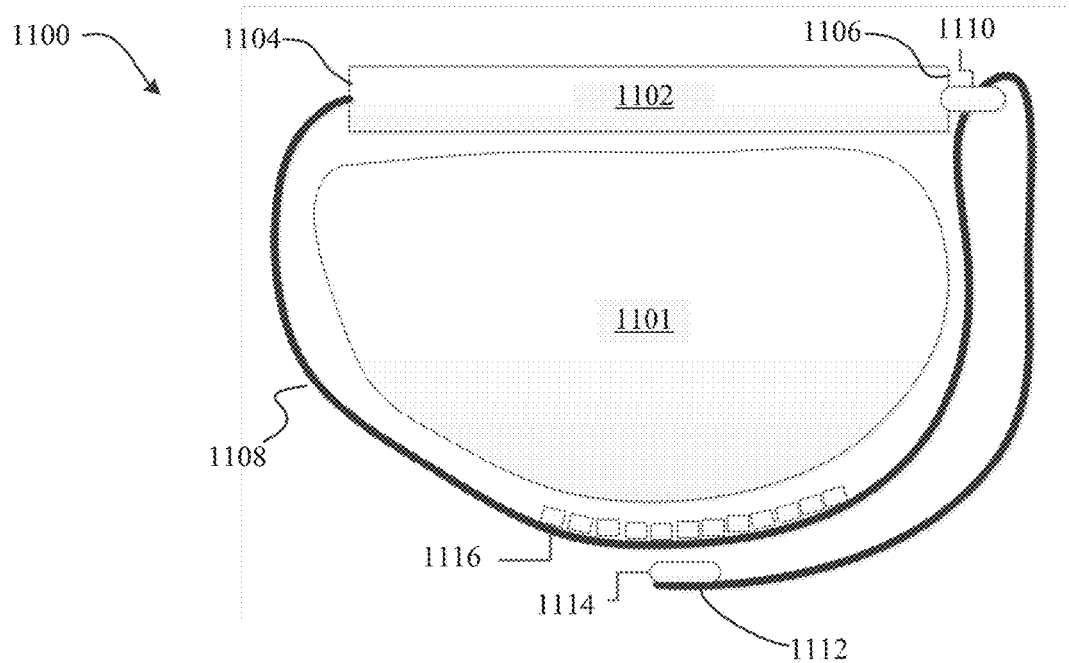
FIG. 11 illustrates an exemplary device for detecting a band configuration, estimating a wrist circumference, and/or estimating a target artery depth according to some embodiments of the present disclosure.

FIG. 11 illustrates an exemplary device 1100 for detecting a band configuration/estimating a wrist circumference, and/or estimating a target artery depth according to some embodiments of the present disclosure. Device 1100 may include a device body 1102 having a first side 1104 and a second side 1106. A band 1108 may be coupled with the first side 1104 of device body 1102 and a band loop 1110 may be coupled with the second side 1106 of device body 1102. The band 1108 may be configured to be fed through the band loop 1110 on the second side 1106 of the device body 1102. Thereafter, the free end 1112 of the band 1108 may be folded back to couple with a portion of the band 1108. In some embodiments the device 1100 may include one or more sensors for determining a band configuration of device 1100. The one or more sensors may include a plurality of sensors 1116 disposed along a length of the band 1108. The sensors 1116 may be configured to detect the free end 1112 of the band 1108 when the free end 1112 folds back and couples with a portion of the band 1108. For example, as illustrated, a magnet 1114 may be disposed at the free end 1112 of the band 1108. The plurality of sensors 1116 disposed along a length of the band 1108 may be magnetic sensors (e.g., hall effect sensors or the like) that are configured to detect the magnet 1114 at the free end 1112 of the band 1108. The detection of the free end 1112 of the band 1108 may be used to determine a length of band needed to couple the device 1100 to the wrist 1101 of the user. In other embodiments, the a sensor may be disposed at the band loop 1110 that is configured to determine a length of band 1108 that is fed through the loop 1110. This information may be used in the alternative or in the addition to the location of the free end 1112 of the band 1108 to estimate the wrist circumference of the user.

Similar to the embodiments described above, the band configuration/estimated wrist circumference may then be used to estimate the target artery depth. This may be performed for example, by using look up tables based on anthropometric data. In some embodiments, an algorithm may be provided based on test data that relates a target artery depth to a wrist circumference. Thereafter a correction factor based on the band configuration/estimated wrist circumference and/or the estimated target artery depth may be used with pressure signals from the pressure sensor to calculate a blood pressure value to provide for a more accurate blood pressure measurement 1010.

Figure 12:
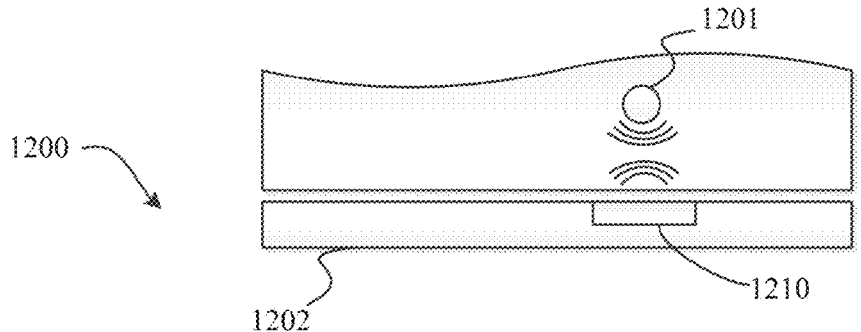
FIG. 12 illustrates an exemplary device for determining an artery depth according to some embodiments of the present disclosure.

In some embodiments, the depth of the radial artery may be measured directly. For example, as illustrated in FIG. 12, a wrist-worn device 1200 may include an ultrasound transducer 1210 coupled with a band 1202 of the device 1200. The ultrasound transducer 1210 may be configured to direct ultrasound energy toward the target artery 1201. The ultrasound transducer 1210 may be further configured to receive reflected ultrasound energy from the target artery 1201 to determine a depth of the target artery 1201. Alternatively, a separate ultrasound transducer may be configured to receive the ultrasound energy. Again, after determining a depth, an error correction factor based on depth may be determined. The correction factor may then be used with the pressure signals from the pressure sensor to calculate a blood pressure value associated with the user.

Figure 13:
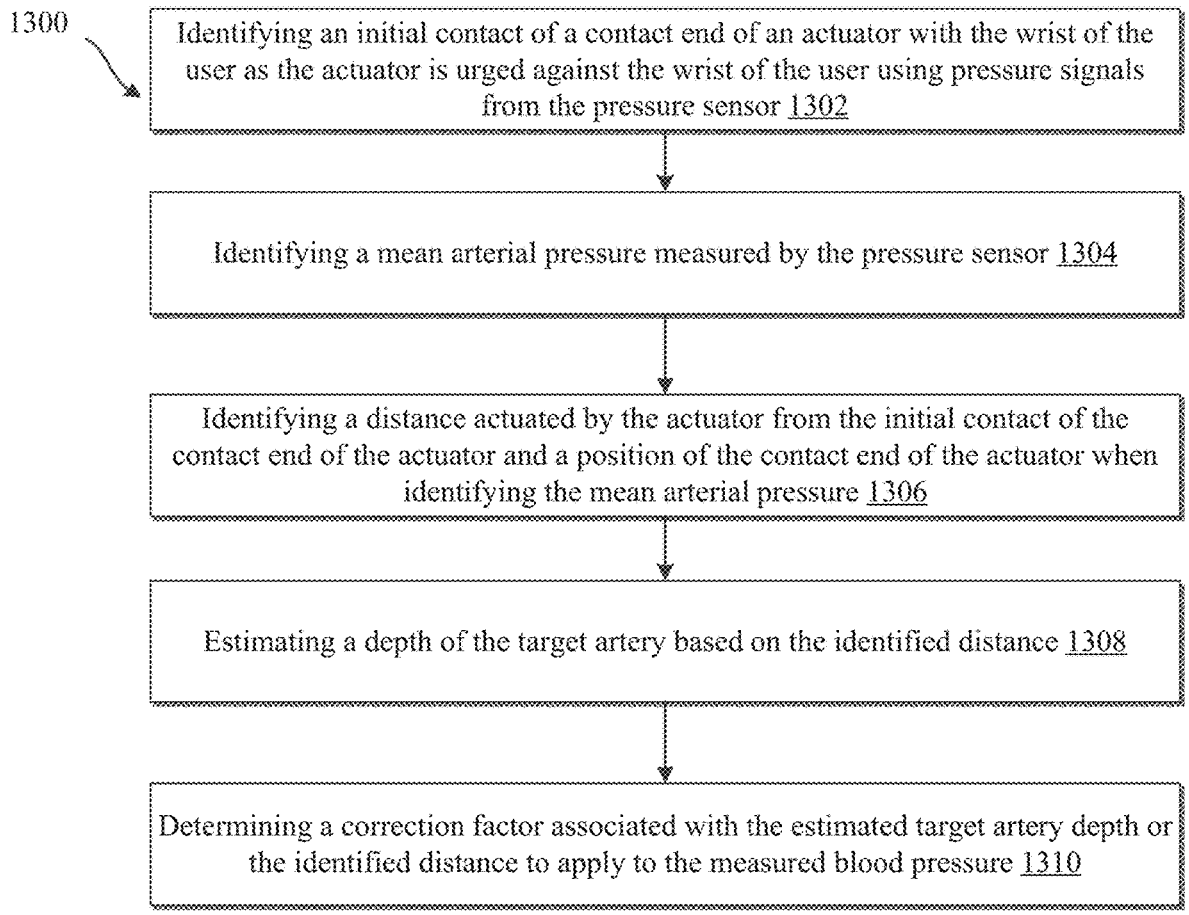
FIG. 13 illustrates an exemplary method for determining a correction factor associated with an estimated target artery depth to apply to a measured blood pressure according to some embodiments of the present disclosure.

In other embodiments, a target artery may be estimated based in part on an actuation distance by an actuator. For example, FIG. 13 illustrates an exemplary method 1300 for determining a correction factor associated with an estimated target artery depth to calculate or factor into a blood pressure value according to some embodiments of the present disclosure. Method 1300 may start with identifying an initial contact of a contact end of an actuator with the wrist of the user as the actuator is urged against the wrist of the user using pressure signals from a pressure sensor 1302. A mean arterial pressure may be identified by the pressure sensor 1304. The method may proceed by identifying distance actuated by the actuator from the initial contact of the contact end of the actuator and a position of the contact end of the actuator when identifying the mean arterial pressure 1306. The depth of the target artery may be estimated based on the identified distance 1308. Thereafter, a correction factor may be determined that is associated with the estimated target artery depth or the identified distance for application to the measured blood pressure 1310. The correction factor may adjust for errors that may arise with deeper arteries.

Figure 14:
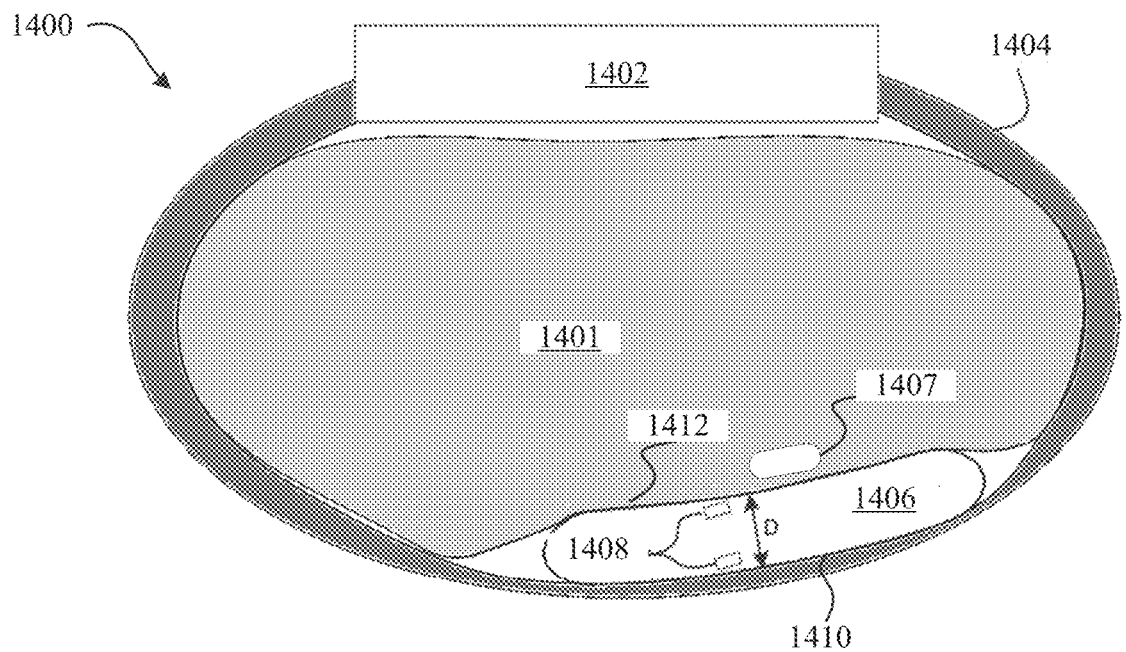
FIG. 14 illustrates an exemplary device for estimating target artery depth according to some embodiments of the present disclosure.

FIG. 14 illustrates an exemplary device 1400 for estimating target artery depth according to some embodiments of the present disclosure. Device 1400 may include a device body 1402 that couples with the wrist 1401 of the user via band 1404. The band 1404 may support an actuator 1406 proximate the target artery 1407 when the device 1400 is coupled with the wrist of the user. One or more sensors 1408 may be provided that are configured to measure a parameter associated with an actuation amount of the actuator 1406 to determine a distance actuated D by the actuator 1406

Band 1404 may be one or more bands configured to couple around the wrist of the user. The actuator 1406 may be a fluid bladder in some embodiments. While illustrated as a fluid bladder, it should be understood that actuator 1406 may be a linear actuator in other embodiments. The one or more sensors 1408 may be a linear actuator in other embodiments. In some embodiments, at least one sensor 1408 may be a pressure sensor. Additionally while illustrated with sensors 1408 coupled with an interior of the actuator 1406, it should be understood that a pressure sensor may be coupled to an external surface of the actuator 1406. The pressure sensor may detect (e.g., with a change in pressure) an initial contact with a contact end 1412 of the actuator 1406 to the skin. Thereafter, after the actuator 1406 has been actuated to be urged against the wrist of the user by a distance D, the pressure sensor may measure a mean arterial pressure. In at least some embodiments, the distance actuated D when the device 1400 measures a mean arterial pressure may be associated with the target artery depth. This estimated target artery depth may then be used to calculate a correction factor for application to the measured blood pressure to provide an adjusted blood pressure measurement.

Accordingly, the one or more sensors 1408 may include an optical, acoustic, magnetic, or fluid flow sensor according to some embodiments. For example, sensors 1408 may include an optical or acoustic sensor configured to direct energy from a proximal end 1410 of bladder 1406 to a contact end 1412 of bladder 1406 to determine an actuation distance D of bladder 1406. As used herein, the terms "proximal" and "distal" are to be taken as relative to the skin-engaging surface of the wearable device. For example, "distal" is to be understood as relatively close to the skin-engaging surface of device or toward the skin of the user. "Proximal" is to be understood as relatively further from the skin-engaging surface of the device or a direction away from the skin of the user when the device is coupled with the user. In some embodiments, another sensor optical and or acoustic receiver may be disposed at the contact end 1412 of the fluid bladder 1406 to receive the energy directed by the corresponding optical or acoustic sensor on the proximal end 1410 of the bladder. Optionally, the optical or acoustic sensor may be configured to reflect energy off the contact end 1412 of the bladder 1406 in order to determine the actuation distance D.

In some embodiments, an optical sensor may be configured to project an optical pattern on to an opposing surface 1410, 1412 and the reflected pattern may be detected and indicative of the actuation distance D between the opposing surfaces 1410, 1412.

In alternative embodiments, the sensors 1408 may include a magnetic sensor (e.g., hall effect sensor) on one of surfaces 1410, 1412, and a magnet disposed on the opposite surface 1412, 1410. The magnetic sensor may detect a change in magnetic force due to an increasing distance between the magnet and the magnetic sensor during actuation of the actuator 1406. The change in magnetic force may be used to calculate an actuation distance D of the actuator 1406.

In still further embodiments, sensors 1408 may include a fluid flow sensor. A fluid flow sensor may be configured to measure the volume of fluid (e.g., air or the like) delivered into the bladder 1406. The volume of fluid measured may be used to determine the actuation distance D (e.g., with the use of bladder configuration and fluid property or the like). In some embodiments, a look up table may be provided for associating a delivered fluid volume with an actuation distance. In some embodiments, an algorithm may be provided based on the bladder configuration and fluid to determine the actuation distance D. After estimating the depth based on the actuation depth of the actuator, an error correction factor based on depth may be determined. The correction factor may then be applied to the measured blood pressure to provide for a corrected blood pressure measurement.

Figure 15:
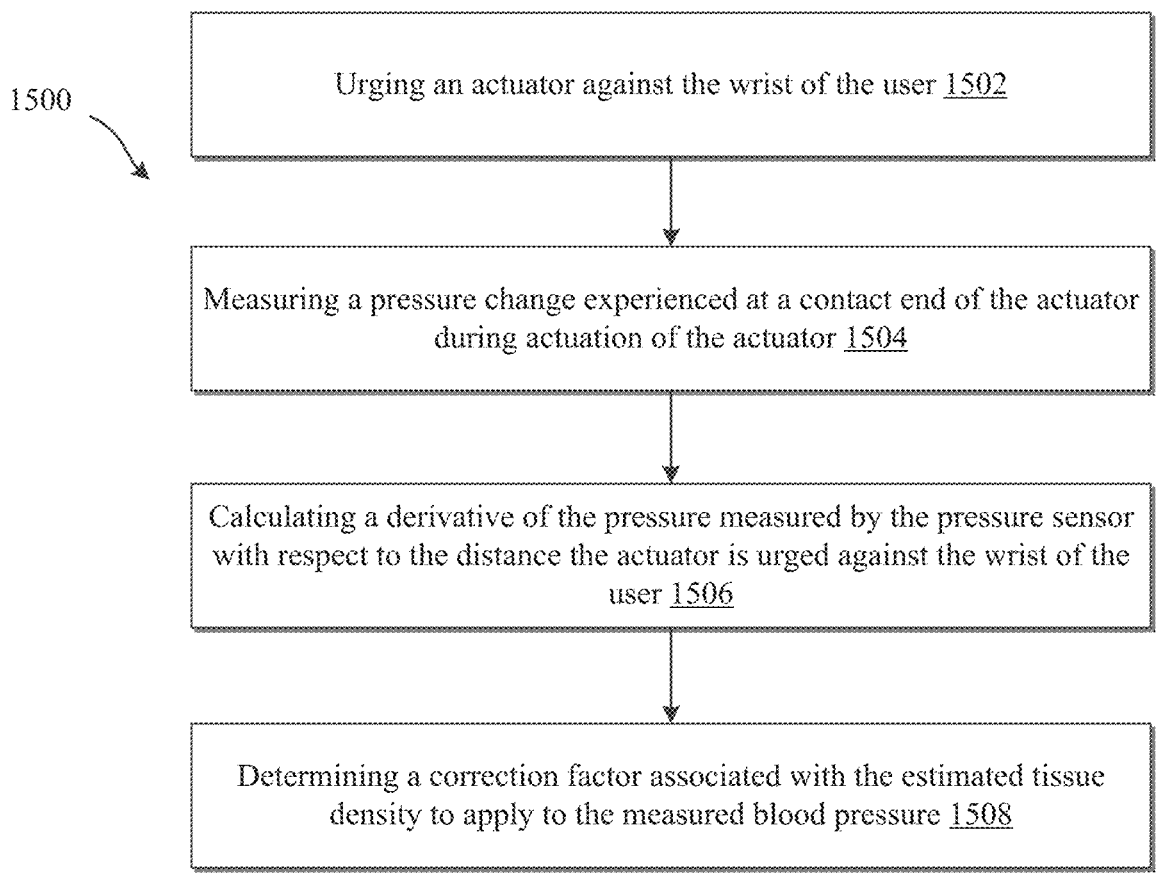
FIG. 15 illustrates an exemplary method for determining a correction factor associated with an estimated tissue density or hydration to apply to a measured blood pressure according to some embodiments of the present disclosure.

As discussed above, the amount of dispersion of the applied pressure within the tissue may be correlated to a composition or a hydration of the tissue disposed between the actuator and the target artery. Thus in some embodiments, a tissue density may be estimated and a correction factor may be applied to a measured blood pressure to account for the variation in tissue composition and/or hydration between user to user or between consecutive measurements from the same user. Thus sensors may be provided to measure parameters that are indicative of the tissue density and/or hydration of the user. For example, a change in pressure may be measured as the actuation depth is changed (dP/dZ). FIG. 15 illustrates an exemplary method 1500 for determining a correction factor associated with an estimated tissue density or hydration to apply to a measured blood pressure according to some embodiments of the present disclosure. At step 1502 a actuator may be urged against the wrist of the user. A pressure change experienced at the contact end of the actuator may be measured during actuation of the actuator 1504. At 1506, the method 1500 may include calculating a derivative (dP/dZ) of the pressure measured by the pressure sensor with respect to the distance the actuator is displaced against the wrist of the user. A correction factor may then be determined 1508 that is associated with the estimated tissue density. The correction factor may then be used with the pressure signals from a pressure sensor to calculate a blood pressure value. Any of the embodiments of the wrist-worn device described above may be configured to carry out the method 1500.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of embodiments of the present disclosure is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Different arrangements of the components depicted in the drawings or described above, as well as components and steps not shown or described are possible. Similarly, some features and sub-combinations are useful and may be employed without reference to other features and sub-combinations. Embodiments of the disclosure have been described for illustrative and not restrictive purposes, and alternative embodiments will become apparent to readers of this patent. Additionally, it should be understood that the ranges and materials provided herein are exemplary and that the ultimate selection of sizes, materials, etc. may depend on the overall device design and application. Accordingly, the present disclosure is not limited to the embodiments described above or depicted in the drawings, and various embodiments and modifications may be made without departing from the scope of the claims below.

What is claimed is:
1. A wrist-worn device comprising:
a device housing;
one or more bands coupled with the device housing, the one or more bands having a plurality of band configurations configured to accommodate a range of wrist sizes, the one or more bands comprising one or more band configuration sensors that generate a band configuration output indicative of which of the plurality of band configurations is a current configuration of the one or more bands utilized for coupling the device housing to a wrist;
a pressure sensor coupled with the one or more bands, the pressure sensor configured to measure a pressure signal; and a processor coupled with the pressure sensor and the one or more band configuration sensors, the processor being configured to:
process the band configuration output to detect the current configuration of the one or more bands;
correlate the current configuration of the one or more bands to a circumference of the wrist; and
calculate a blood pressure value using the pressure signal from the sensor and a correction factor based on the circumference of the wrist.

2. The wrist-worn device of claim 1, wherein the one or more bands have a width less than 3 cm.

3. The wrist-worn device of claim 1, wherein the one or more bands comprises a first band and a second band configured to couple with the first band, wherein the first band includes a plurality of notches and the second band includes a latch configured to couple with one of the plurality of notches of the first band, and wherein the band configuration output is indicative of which notch out of the plurality of notches is coupled with the latch.

4. The wrist-worn device of claim 3, wherein the band configuration output is indicative of a completed circuit formed via coupling of the latch with one of the plurality of notches.

5. The wrist-worn device of claim 4, wherein the plurality of notches comprise a metal ring for forming part of the completed circuit.

6. The wrist-worn device of claim 3, wherein the latch interrupts an optical signal at the notch that the latch is coupled with and wherein the band configuration output is indicative of interruption of the optical signal at the notch coupled with the latch.

7. The wrist-worn device of claim 3, wherein the latch comprises a magnetic material and wherein the one or more band configuration sensors comprise magnetic sensors, each of the magnetic sensors being associated with one of the plurality of notches, and wherein the band configuration output is indicative of the magnetic material of the latch being detected by one of the magnetic sensors.

8. The wrist worn device of claim 1, wherein the one or more bands comprises a single band having a first end and a second end opposite the first end; wherein the first end of the band is coupled with a first side of the device housing and the second end of the band is configured to be fed through a band loop on a second side of the device housing, wherein the band configuration output is indicative of a length of band fed through the band loop.

9. The wrist-worn device of claim 8, wherein the band is configured to fold back on itself after being fed through the band loop with the second end of the band configured to couple with a portion of the band and wherein the band configuration output is indicative of a location of the second end of the band along a length of the band.

10. The wrist-worn device of claim 9, wherein the second end of the band is configured to couple with the portion of the band via magnetic attraction.

11. The wrist-worn device of claim 10, wherein the one or more band configuration sensors comprise magnetic sensors disposed along the length of the band for detecting the location of the second end of the band along the length of the band.

12. A method of calculating a blood pressure value of a user with a device having a device housing and one or more bands coupled with the device housing and configured to wrap around a portion of a wrist of the user to couple the device housing to the wrist of the user, the one or more bands being configured to couple with the wrist of the user using one of a plurality of band configurations configured to accommodate a range of wrist sizes, the one or more bands comprising one or more band configuration sensors, the method comprising:
generating, via the one or more band configuration sensors, a band configuration output indicative of which of the plurality of band configurations is a current configuration of the one or more bands utilized for coupling the device housing to the wrist of the user;
measuring a pressure signal from the user with a pressure sensor coupled with the one or more bands of the device;
processing, via a device processor, the band configuration output to identify the current configuration of the one or more bands;
correlating, by the device processor, the current configuration of the one or more bands to a circumference of the wrist of the user;
calculating, by the device processor, a blood pressure value using the pressure signal from the pressure sensor and a correction factor based on the circumference of the wrist of the user; and
outputting, by the device processor, the calculated blood pressure value.

13. The method of claim 12, wherein the one or more bands comprises a first band and a second band configured to couple with the first band to couple the device housing to the wrist of the user, wherein the first band includes a plurality of notches and the second band includes a latch configured to couple with one of the plurality of notches of the first band, and wherein the band configuration output is indicative of which notch out of the plurality of notches is coupled with the latch.

14. The method of claim 13, wherein the band configuration output is indicative of a completed circuit formed via coupling of the latch with one of the plurality of notches.

15. The method of claim 13, wherein the band configuration output is indicative of interruption of an optical signal by the latch at the notch coupled with the latch.

16. The method of claim 13, wherein:
the one or more band configuration sensors comprise magnetic sensors;
each of the magnetic sensors is associated with one of the plurality of notches; and
the generation of the band configuration output comprises detecting a magnetic material of the latch via one of the magnetic sensors.

17. The method of claim 12, wherein the one or more bands comprises a single band having a first end and a second end opposite the first end; wherein the first end of the band is coupled with a first side of the device housing and the second end of the band is configured to be fed through a band loop on a second side of the device housing; and wherein the band configuration output is indicative of a length of band fed through the band loop.

18. The method of claim 17, wherein the band is configured to fold back on itself after being fed through the band loop with the second end of the band configured to couple with a portion of the band and wherein the band configuration output is indicative of a location of the second end of the band along a length of the band.

* * * * *